(12) United States Patent
Roy et al.

(10) Patent No.: US 11,026,589 B2
(45) Date of Patent: Jun. 8, 2021

(54) DYNAMIC RECOMMENDATIONS OF SENSORS FOR PATIENT MONITORING

(71) Applicant: International Business Machines Corporation, Armonk, NY (US)

(72) Inventors: Subhrajit Roy, Melbourne (AU); Filiz Isabell Kiral-Kornek, Southbank (AU); Stefan Harrer, Melbourne (AU); Benjamin Scott Mashford, Southbank (AU); Mahtab Mirmomeni, Melbourne (AU)

(73) Assignee: INTERNATIONAL BUSINESS MACHINES CORPORATION, Armonk, NY (US)

(*) Notice: Subject to any disclaimer, the term of this patent is extended or adjusted under 35 U.S.C. 154(b) by 215 days.

(21) Appl. No.: 16/160,058

(22) Filed: Oct. 15, 2018

(65) Prior Publication Data

US 2020/0113443 A1 Apr. 16, 2020

(51) Int. Cl.
*A61B 5/0205* (2006.01)
*A61B 5/00* (2006.01)
*G16H 10/20* (2018.01)
*G16H 10/60* (2018.01)

(52) U.S. Cl.
CPC .......... *A61B 5/0205* (2013.01); *A61B 5/0006* (2013.01); *A61B 5/6802* (2013.01); *A61B 5/6898* (2013.01); *A61B 2560/0209* (2013.01); *A61B 2560/0214* (2013.01); *A61B 2562/0219* (2013.01); *A61B 2562/0271* (2013.01); *G16H 10/20* (2018.01); *G16H 10/60* (2018.01)

(58) Field of Classification Search
USPC ....................................................... 705/2–3
See application file for complete search history.

(56) References Cited

U.S. PATENT DOCUMENTS

| | | | |
|---|---|---|---|
| 9,649,055 B2 | 5/2017 | Ashe et al. | |
| 9,990,026 B1 | 6/2018 | Kahn et al. | |
| 2005/0113704 A1 | 5/2005 | Lawson et al. | |
| 2014/0188402 A1 | 7/2014 | Garcia et al. | |
| 2015/0130633 A1* | 5/2015 | Grubstein | A61B 5/743 340/870.07 |
| 2015/0359429 A1 | 12/2015 | Al-Ali et al. | |
| 2016/0317088 A1 | 11/2016 | Fougere et al. | |
| 2017/0196497 A1* | 7/2017 | Ray | A61B 5/11 |
| 2019/0172579 A1* | 6/2019 | Peterson | G16H 40/67 |

OTHER PUBLICATIONS

Mel, et al. "The NIST Definition of Cloud Computing". Recommendations of the National Institute of Standards and Technology. Nov. 16, 2015.

* cited by examiner

*Primary Examiner* — Jonathan Durant
*Assistant Examiner* — Benjamin L. Hanks
(74) *Attorney, Agent, or Firm* — Joseph Petrokaitis, Esq.; McGinn I.P. Law Group, PLLC

(57) ABSTRACT

A recommendation method, system, and computer program product include monitoring a patient using a plurality of sensors, receiving patient information including a comfort level corresponding to a sensor of the plurality of sensors, determining a relevance of each sensor of the plurality of sensors to at least one health conditions of the patient, and determining at least one sensor of the plurality of sensors to disconnect based on the comfort level and the relevance of each sensor.

19 Claims, 6 Drawing Sheets

DYNAMIC RECOMMENDATIONS OF SENSORS FOR PATIENT MONITORING

BACKGROUND

The present invention relates generally to a recommendation method, and more particularly, but not by way of limitation, to a system, method, and computer program product to dynamically recommend the use of sensors for patient monitoring.

Patient comfort is one of the most critical issues during clinical trials. A study that is perceived as too intrusive may result in fewer patients being willing to sign up or patients dropping out over the course of the study. On one hand, this can lead to a selection bias, where only patients with the very severe cases of a disease enroll in studies, which makes incremental improvements of general drugs difficult. On the other hand, if patients drop out of studies, valuable data is lost and the study may be in danger of not being meaningful. While the introduction of more and more sensors into clinical trials enables a capture of rich and meaningful data, there is a risk of overburdening study participants.

Electronic devices for monitoring the health of patients include a variety of sensors. These components can capture and analyze a wide range of sensory input (e.g., motion, skin conductance, audio, video, etc.).

Conventional techniques require all sensors to be active throughout the entire testing phase. Other conventional techniques cannot handle an error in a sensor due to a deliberate disconnect or a faulty sensor.

Therefore, a new technique is needed for a machine learning system that prioritizes patient comfort to handle missing sensors and/or purposively turn off sensors to increase the comfort the patient.

SUMMARY

In an exemplary embodiment, the present invention provides a method including monitoring a patient using a plurality of sensors, receiving patient information including a comfort level corresponding to a sensor of the plurality of sensors, determining a relevance of each sensor of the plurality of sensors to at least one health conditions of the patient, and determining at least one sensor of the plurality of sensors to disconnect based on the comfort level and the relevance of each sensor. One or more other exemplary embodiments include a computer program product and a system, based on the method described above.

Other details and embodiments of the invention will be described below, so that the present contribution to the art can be better appreciated. Nonetheless, the invention is not limited in its application to such details, phraseology, terminology, illustrations and/or arrangements set forth in the description or shown in the drawings. Rather, the invention is capable of embodiments in addition to those described and of being practiced and carried out in various ways and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

BRIEF DESCRIPTION OF THE DRAWINGS

Aspects of the invention will be better understood from the following detailed description of the exemplary embodiments of the invention with reference to the drawings, in which.

DETAILED DESCRIPTION

Figure 1:
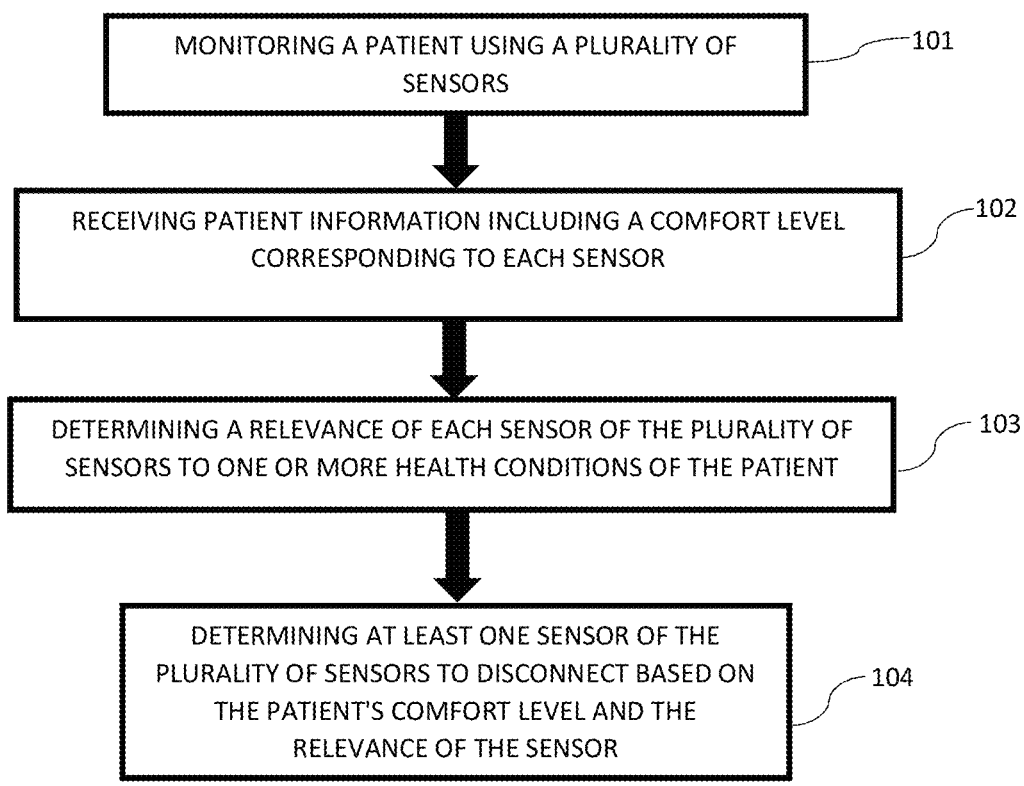
FIG. 1 exemplarily shows a high-level flow chart for a recommendation method 100 according to an embodiment of the present invention.

The invention will now be described with reference to FIGS. 1-6, in which like reference numerals refer to like parts throughout. It is emphasized that, according to common practice, the various features of the drawing are not necessarily to scale. On the contrary, the dimensions of the various features can be arbitrarily expanded or reduced for clarity.

By way of introduction of the example depicted in FIG. 1, an embodiment of a recommendation method 100 according to the present invention can include various steps for a multi-modal, accurate, and robust healthcare monitoring system that includes a mechanism to both, increase patient comfort over time, and harness valuable data for classification should a patient decide to switch sensors off.

Thus, the invention can use a generative classifier in combination with a discriminative classifier as a failsafe in case of missing inputs which allows the invention to make predictions in the face of sensor failures or sensor disconnections. And, over time, the output of the generative classifier is analyzed to turn sensors on or off in a personalized way thereby increasing patient comfort.

Figure 4:
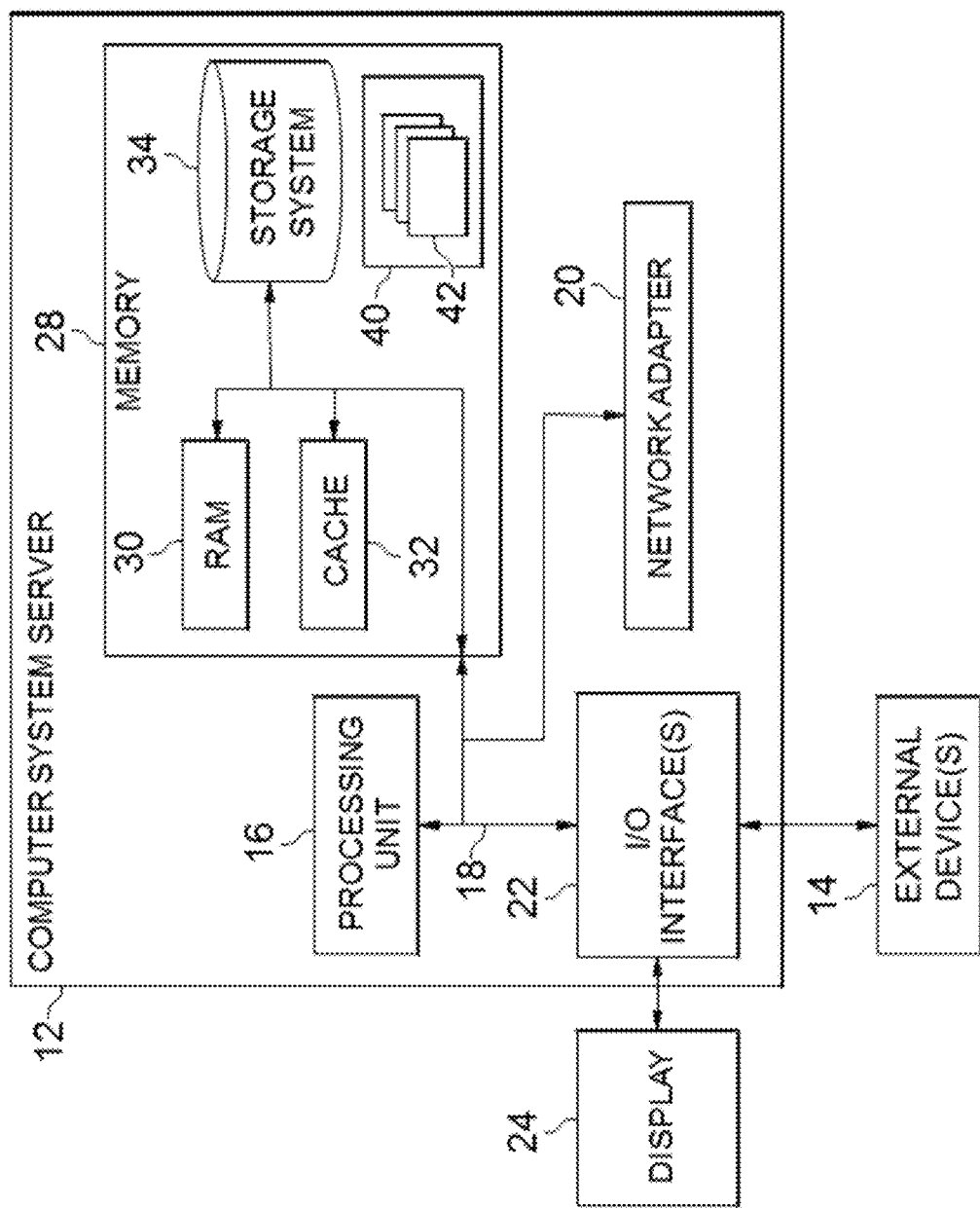
FIG. 4 depicts a cloud-computing node 10 according to an embodiment of the present invention.

By way of introduction of the example depicted in FIG. 4, one or more computers of a computer system 12 according to an embodiment of the present invention can include a memory 28 having instructions stored in a storage system to perform the steps of FIG. 1.

Although one or more embodiments may be implemented in a cloud environment 50 (e.g., FIG. 6), it is nonetheless understood that the present invention can be implemented outside of the cloud environment.

Referring generally to FIG. 1, the method 100 includes various steps for improving a patient's discomfort level during clinical testing by removing some sensors.

More specifically, in step 101, a patient is monitored using a plurality of sensors. The method 100 receives input signal streams captured simultaneously from various sensors that can include an electroencephalogram (EEG) sensor, an electrodermal activity (EDA) sensor, a photoplethysmogram (PPG) sensor, a video input, an audio input, an electrocardiogram (ECG) sensor, a temperature sensor, an accelerometer sensor, etc. The inputs signals are then fed into a machine learning system 250/350 (see FIGS. 2 and 3) as described later.

In step 102, patient information is received including comfort level corresponding to each sensor. For example, the patient may find that the temperature sensor is uncomfortable due to an injury whereas the EDA sensor may not be noticeable.

In step 103, a relevance of each sensor of the plurality of sensors to one or more health conditions of the patient is determined.

Figure 2:
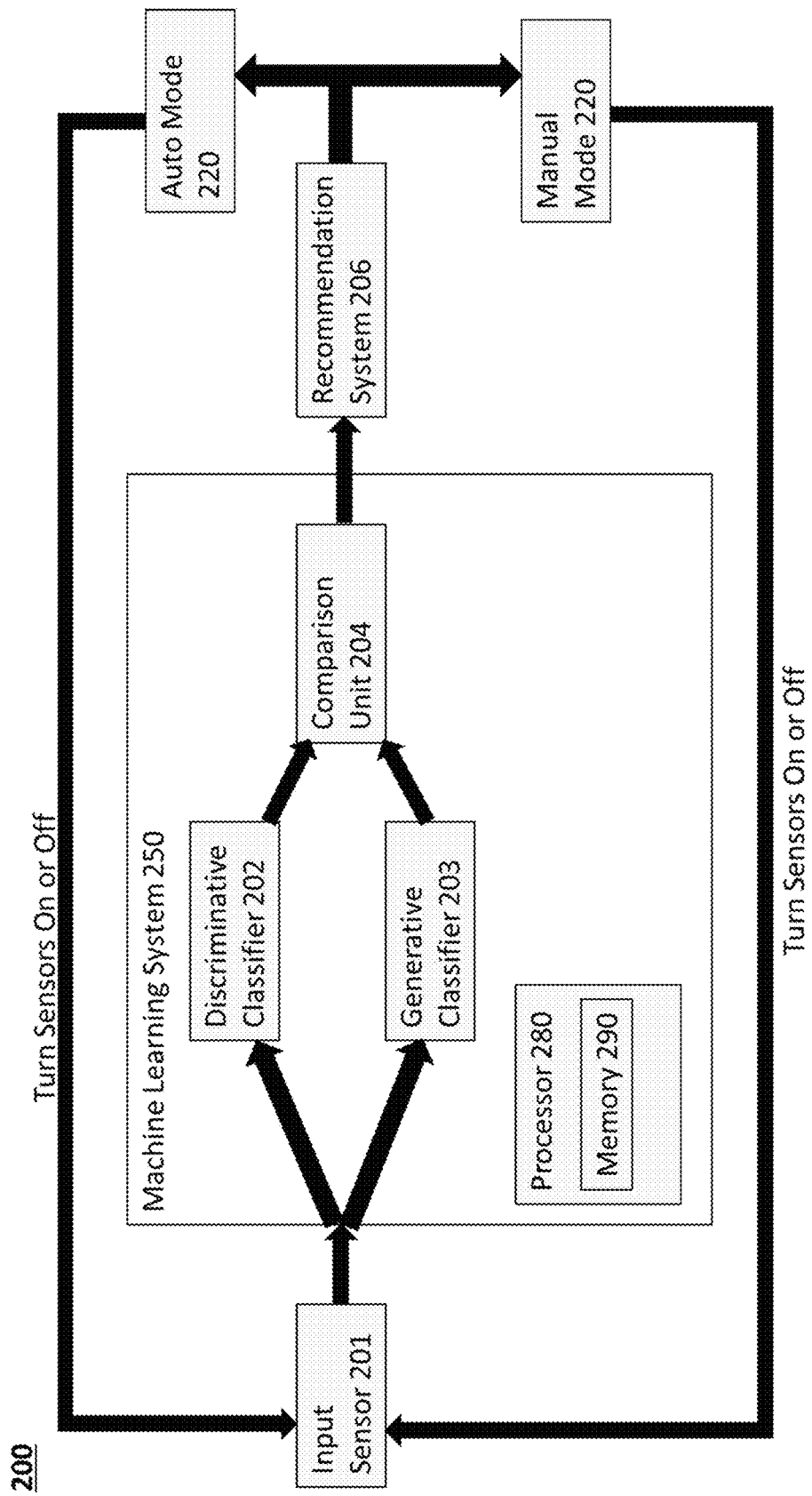
FIG. 2 exemplarily depicts a system architecture 200 of a machine learning system 250 according to an embodiment of the present invention.

With reference to FIG. 2, FIG. 2 depicts a system architecture 200 for training a machine learning system 250 that includes a discriminative classifier 202, a generative classifier 203, and a comparison unit 204. It is noted that the system 250 includes a processor 280 and a memory 290 that stores instructions to cause the processor to operate the classifiers 202 and 203 and the comparison unit 204. Inputs 201 are deliberately turned off in a systematic way for the generative classifier 203. Next, its performance is compared to the discriminative classifier 202. For a particular patient for a given sensor 201, if the performance is similar, then either the sensor is turned off or a recommendation 206 is sent to the patient, their clinician, or their care-givers.

More specifically, during training, the sections of the collected data from the input sensor 201 where all features are present are selected for training both the generative classifier 203 and the discriminative classifier 202. However, the data for which some features are absent are included only in the training set for the generative classifier 203 but not for the discriminative classifier. This is because by its nature discriminative classifiers are not able to handle missing inputs during training. On the other hand, generative classifiers are able to use techniques such as expectation maximization to tackle missing inputs during training. Therefore, the machine learning system 250 is trained for how each input sensor effects the patient by comparing via the comparison unit 204 the results from all the sensors being active (i.e., output from the discriminative classifier 202) with missing sensors from an output from the generative classifier 203. The relevance of each sensor for step 103 of the method 100 is determined based on the output of the comparison unit 204.

In other words, the discriminative classifier 202 depends on all of the features of the data being present i.e. when all of the sensors are turned on. This is because during the training stage the discriminative classifier 202 has been trained on data from all sensors and hence during test time to make a prediction it expects data from all sensors. On the other hand, the generative classifier 203 can work even in the absence of one or more features during test time. The generative classifier does so by learning a joint distribution of the input features and the labels and by marginalizing the missing features during testing.

For example, if there is a difference in performance data less than a predetermined threshold amount between the sensor being on or off, the relevance is low and the sensor can be removed. Further, the recommendation system 206 receives the result of the comparison from the comparison unit 204.

And, it is noted that the system 250 trains itself either in an auto mode 220 which selectively turns on and off sensors based on the result from the comparison unit 204 and instructions from the recommendation system 206 to test each combination of sensors for the patient. Alternatively, a manual mode 220 can be activated to test specific combinations of sensors. For example, if there are five sensors, the system will be first tested with all five sensors and then each sensor removed to have a different combination of sensors and the comparison unit 204 outputs the difference between the classifiers. That is, analyzing the importance of modalities is performed by systemically dropping features for the generative classifier 203 and comparing its performance with the discriminative classifier 202.

Referring back to FIG. 1, in step 104, at least one sensor of the plurality of sensors is determined to be disconnected based on the patient's comfort level and the relevance of each sensor. That is, the recommendation system 206 recommends which sensors can be turned off based on the comparison between the results from the combination of the discriminative classifier 202 and the generative classifier 203.

Figure 3:
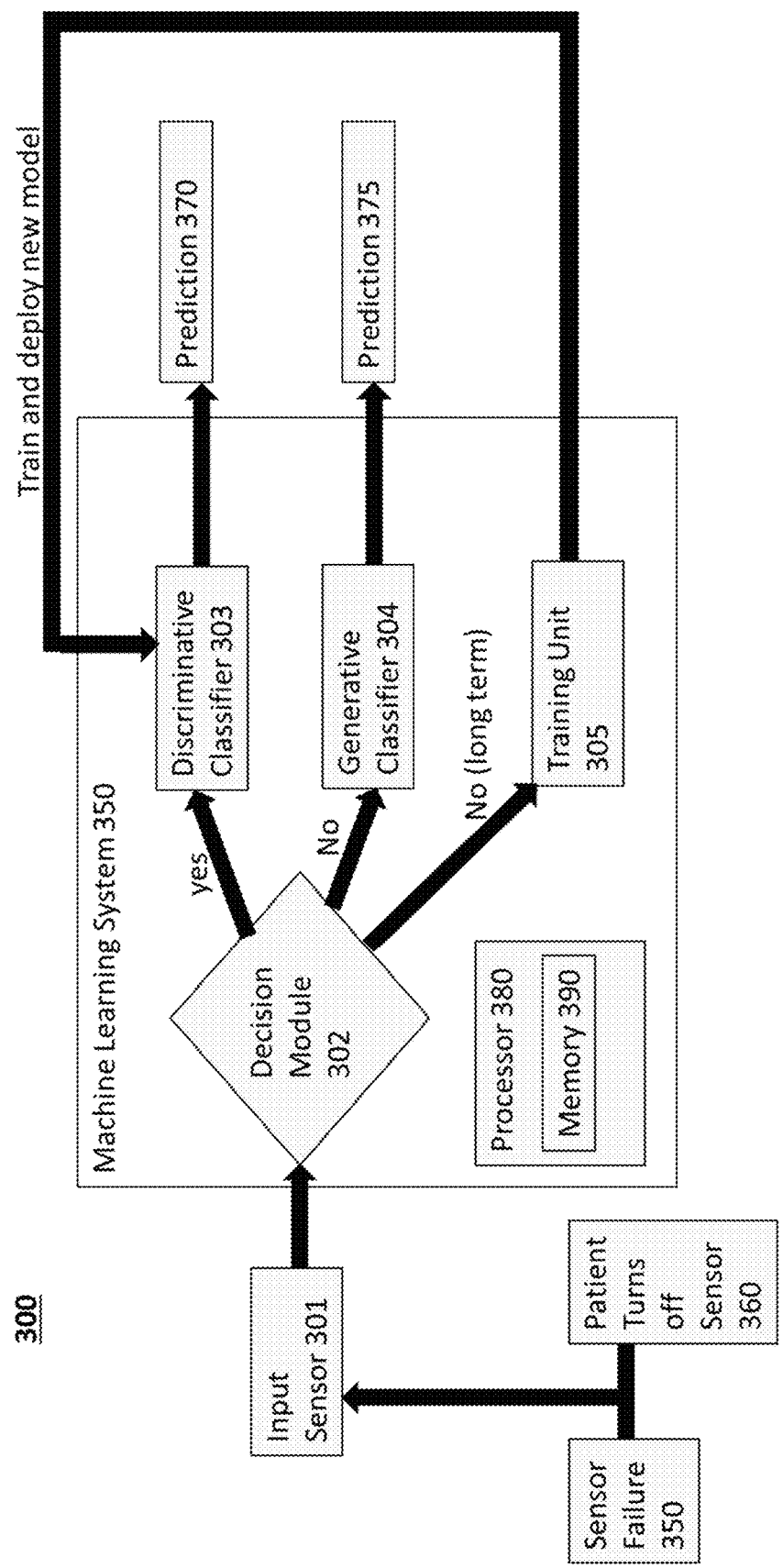
FIG. 3 exemplarily depicts a system architecture 300 of a machine learning system 350 according to an embodiment of the present invention.

Referring generally to FIG. 3, FIG. 3 depicts a testing (i.e., run-time) phase of the method 100. During testing, when data is being streamed, each sample is first evaluated to check whether all features are present. That is, the decision module 302 checks the inputs from the input sensor 301 as to whether each sensor is present. If "Yes", it is passed on to the discriminative classifier 303 for classification and a prediction 370 is output.

If "No", the generative classifier 304 makes a prediction 375 by marginalizing the input. This makes the system robust to sensor failures or sensor disconnections by the patient. Note that, the generative classifier 303 is also capable of making a prediction 370 if all features are present. However, the discriminative classifier 303 takes preference since typically it has a better performance. This makes the system robust to sensor failures 350 and deliberate sensor disconnections 360 by patients. That is, the system 350 passes the inputs to the correct classifier for handling whether all inputs are present or some are missing.

Moreover, the performance of the discriminative classifier 303 and the generative classifier 304 is tracked over time for each patient. If it is revealed upon analysis that the generative classifier 304 can perform as good as the discriminative classifier 303 (e.g., based on training from the system 250) without some of the input features, then either those sensors are turned off or the patient is recommended to take those sensors off. This in turn increases patient comfort (i.e., step 104 of method 100).

Furthermore, the comparison of the performance of the classifiers will also reveal if the patient has disconnected a sensor (such as taking off an EEG cap) that is crucial to the task at hand. In such a case, the patient will be notified to turn the sensor on.

It is noted that the system 350 includes a training unit 305 which can re-train the discriminative classifier 303 when a sensor will be missing long term (e.g., based on the output of step 104). That is, if a sensor can be removed for the rest of clinical testing, the discriminative classifier can be re-trained to run with the missing sensor.

Thereby, the method 100 provides a robust technique in the situation when a patient turns off their sensors i.e. it works even if input from one or more sensors is/are missing. This is crucial since in clinical studies where a high number of sensors are used to monitor the bodily signals of patients, they might get irritated and uncomfortable and choose to turn off some of them. The conventional models analyzing these signals fail in such a scenario. However, the combination of a generative and a discriminative classifier as in the invention allows for the method 100 to handle this type of situation.

Additionally, the method 100 is capable of automatically choosing a personalized set of sensors for a particular patient so that they can turn off sensors that are not needed, thereby making them more comfortable (e.g., based on the comparison unit 204 or predictions 370 and 375). Whether a health monitoring system (e.g., machine learning system and peripheral sensors) becomes useful or not depends on whether the patient is feeling comfortable or not. The invention gradually understands which sensors are important for a particular patient and recommends the patient to turn the others off if they choose to. This in turn increases the patient comfort.

And, the method 100 can handle sensor failures in addition to selectively turning off sensors. That is, the method 100 is robust to sensor failures. In a real-world scenario, one or more sensors that are monitoring a patient might fail for a variety of reasons. In consequence, a method that has been trained on data from all sensors will fail. The invention disclosed herein is capable of handling sensor failures by the combination of a discriminative classifier and generative classifier.

Exemplary Aspects, Using a Cloud Computing Environment

Although this detailed description includes an exemplary embodiment of the present invention in a cloud computing environment, it is to be understood that implementation of the teachings recited herein are not limited to such a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as Follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as Follows:

Software as a Service (SaaS): the capability provided to the consumer is to use the provider's applications running on a cloud infrastructure. The applications are accessible from various client circuits through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as Follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Referring now to FIG. 4, a schematic of an example of a cloud computing node is shown. Cloud computing node 10 is only one example of a suitable node and is not intended to suggest any limitation as to the scope of use or functionality of embodiments of the invention described herein. Regardless, cloud computing node 10 is capable of being implemented and/or performing any of the functionality set forth herein.

Although cloud computing node 10 is depicted as a computer system/server 12, it is understood to be operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, hand-held or laptop circuits, multiprocessor systems, microprocessor-based systems, set top boxes, programmable consumer electronics, network PCs, minicomputer systems, mainframe computer systems, and distributed cloud computing environments that include any of the above systems or circuits, and the like.

Computer system/server 12 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing circuits that are linked through a communications network. In a distributed cloud computing environment, program modules may be located in both local and remote computer system storage media including memory storage circuits.

Referring now to FIG. 4, a computer system/server 12 is shown in the form of a general-purpose computing circuit. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further described below, memory 28 may include a computer program product storing one or program modules 42 comprising computer readable instructions configured to carry out one or more features of the present invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may be adapted for implementation in a networking environment. In some embodiments, program modules 42 are adapted to generally carry out one or more functions and/or methodologies of the present invention.

Computer system/server 12 may also communicate with one or more external devices 14 such as a keyboard, a pointing circuit, other peripherals, such as display 24, etc., and one or more components that facilitate interaction with computer system/server 12. Such communication can occur via Input/Output (I/O) interface 22, and/or any circuits (e.g., network card, modem, etc.) that enable computer system/server 12 to communicate with one or more other computing circuits. For example, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, circuit drivers, redundant processing units, external disk drive arrays, RAID systems, tape drives, and data archival storage systems, etc.

Figure 5:
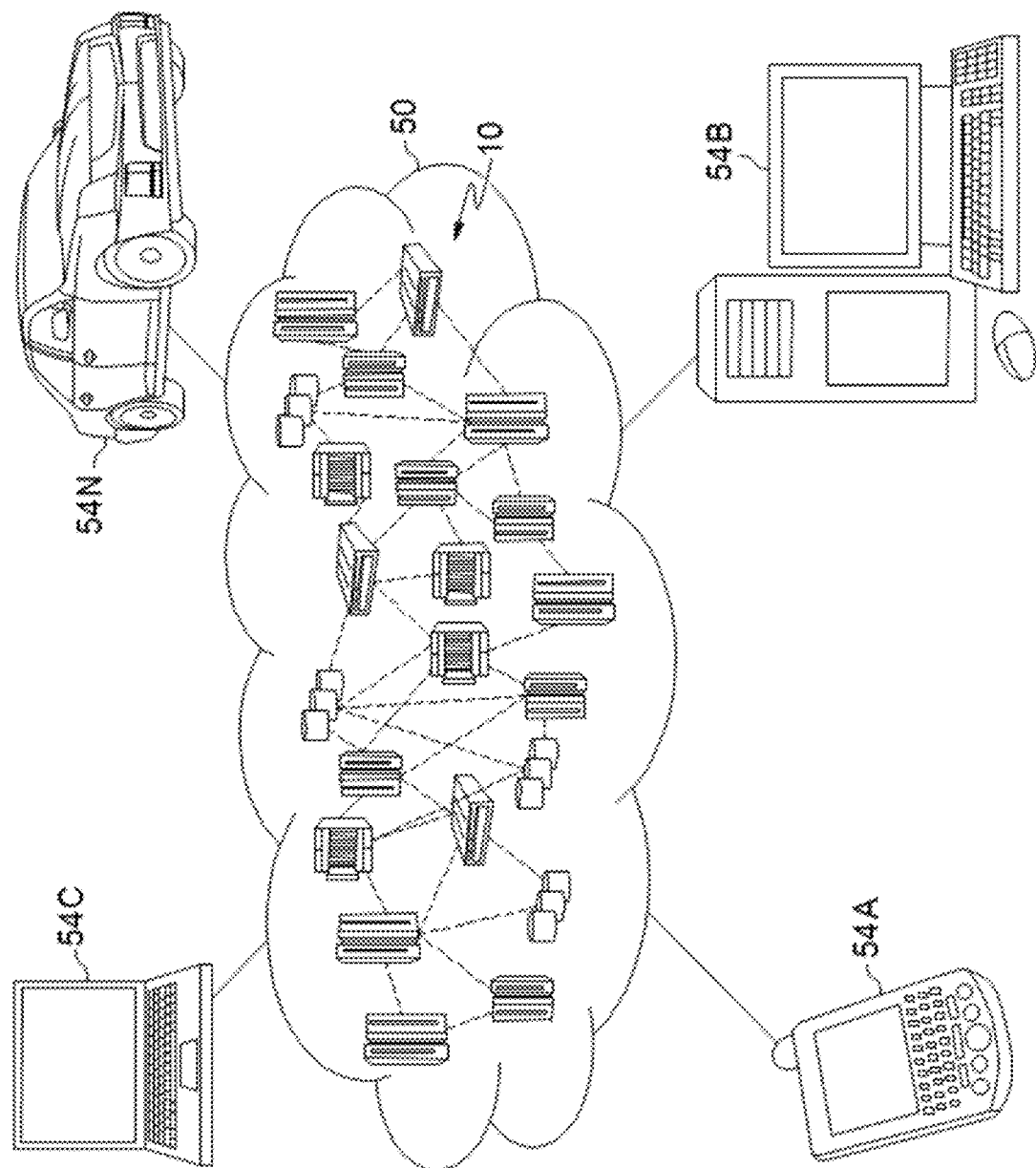
FIG. 5 depicts a cloud-computing environment 50 according to an embodiment of the present invention.

Referring now to FIG. 5, illustrative cloud computing environment 50 is depicted. As shown, cloud computing environment 50 comprises one or more cloud computing nodes 10 with which local computing circuits used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing circuit. It is understood that the types of computing circuits 54A-N shown in FIG. 5 are intended to be illustrative only and that computing nodes 10 and cloud computing environment 50 can communicate with any type of computerized circuit over any type of network and/or network addressable connection (e.g., using a web browser).

Figure 6:
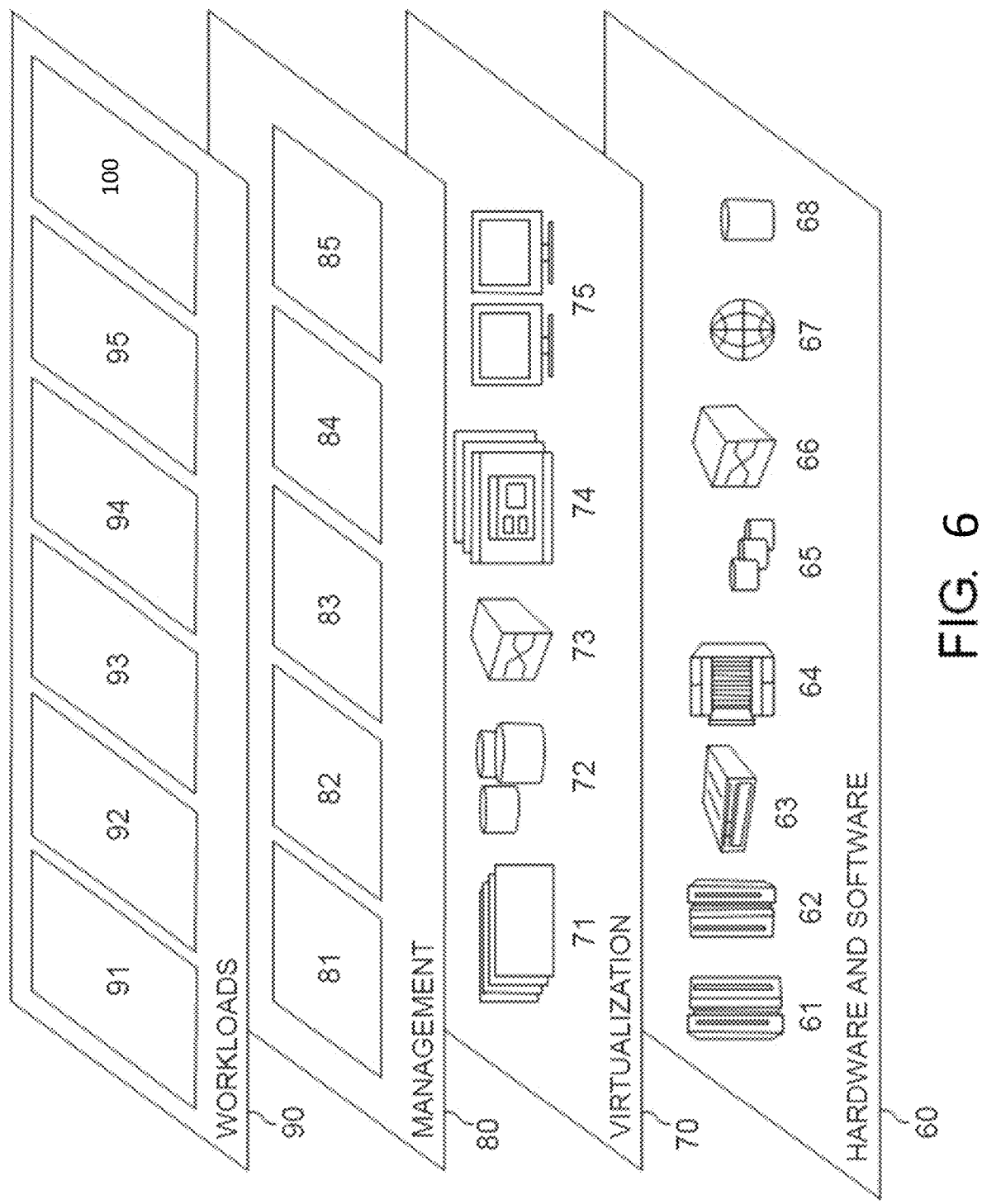
FIG. 6 depicts abstraction model layers according to an embodiment of the present invention.

Referring now to FIG. 6, an exemplary set of functional abstraction layers provided by cloud computing environment 50 (FIG. 5) is shown. It should be understood in advance that the components, layers, and functions shown in FIG. 6 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage circuits 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and recommendation method 100 in accordance with the present invention.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

Further, Applicant's intent is to encompass the equivalents of all claim elements, and no amendment to any claim of the present application should be construed as a disclaimer of any interest in or right to an equivalent of any element or feature of the amended claim.

What is claimed is:

1. A computer-implemented recommendation method, the method comprising:
   monitoring a patient using a plurality of sensors including missing inputs as sensor failures or a sensor disconnection;
   receiving patient information including a comfort level corresponding to a sensor of the plurality of sensors;
   determining a relevance of each sensor of the plurality of sensors to at least one health condition of the patient; and
   determining at least one sensor of the plurality of sensors to disconnect based on the comfort level and the relevance of each sensor, wherein a machine learning system determines the at least one sensor being an optimal sensor,
   wherein a discriminative classifier and a generative classifier are used in combination to operate concurrently with the machine learning system to consider the missing inputs to make a prediction of the relevance of each sensor regardless of the missing inputs,
   further comprising disconnecting the at least one sensor of the plurality of the sensors based on a result of the determining,
   wherein an output of the generative classifier is analyzed to turn off a sensor, and
   wherein the machine learning system is trained by deliberately turning off inputs in a systematic way to train the generative classifier and then a performance after turning off inputs is compared to the discriminative classifier.

2. The computer-implemented method of claim 1, wherein the determining the relevance determines the relevance by:
   obtaining a first output using the discriminative classifier when all of the plurality of sensors transmit the at least one health condition of the patient;
   obtaining a second output using the generative classifier when at least one sensor of the plurality of sensors does not transmit the at least one health condition of the patient; and
   comparing the first output with the second output to determine the relevance of the at least one sensor of the plurality of sensors that does not transmit the at least one health condition of the patient.

3. The computer-implemented method of claim 2, wherein each sensor of the plurality of sensors is deliberately turned off to obtain the second output for the each sensor,
   wherein the comparing compares the first output with the second output for each missing sensor to determine the relevance of the each sensor of the plurality of sensors,
   wherein a sensor of the plurality of sensors is disconnected when the relevance of the sensor is less than a pre-determined threshold value,
   wherein the discriminative classifier is re-trained with a model that does not include the disconnected sensor, and
   wherein the relevance is determined by comparing an output from a combination of the discriminative classifier when all of the plurality of sensors are active and the generative classifier when at least one sensor of the plurality of sensors is not active.

4. The computer-implemented method of claim 1, wherein the relevance is determined by comparing an output from a combination of the discriminative classifier when all of the plurality of sensors are active and the generative classifier when at least one sensor of the plurality of sensors is not active.

5. The computer-implemented method of claim 1, embodied in a cloud-computing environment.

6. The computer-implemented method of claim 1, wherein the output of the generative classifier is analyzed to turn off the sensor in which the turned off sensor is specific to increasing the comfort level,
   wherein the discriminative classifier is re-trained with a model that does not include the disconnected sensor.

7. A computer program product for a recommendation, the computer program product comprising a computer-readable storage medium having program instructions embodied therewith, the program instructions executable by a computer to cause the computer to perform:
   monitoring a patient using a plurality of sensors including missing inputs as sensor failures or a sensor disconnection;
   receiving patient information including a comfort level corresponding to a sensor of the plurality of sensors;
   determining a relevance of each sensor of the plurality of sensors to at least one health condition of the patient; and
   determining at least one sensor of the plurality of sensors to disconnect based on the comfort level and the relevance of each sensor, wherein a machine learning system determines the at least one sensor being an optimal sensor, wherein a discriminative classifier and a generative classifier are used in combination to operate concurrently with the machine learning system to consider the missing inputs to make a prediction of the relevance of each sensor regardless of the missing inputs, further comprising disconnecting the at least one sensor of the plurality of the sensors based on a result of the determining, wherein an output of the generative classifier is analyzed to turn off a sensor, and wherein the machine learning system is trained by deliberately turning off inputs in a systematic way to train the generative classifier and then a performance after turning off inputs is compared to the discriminative classifier.

8. The computer program product of claim 7, wherein the determining the relevance determines the relevance by:

obtaining a first output using the discriminative classifier when all of the plurality of sensors transmit the at least one health condition of the patient;

obtaining a second output using the generative classifier when at least one sensor of the plurality of sensors does not transmit the at least one health condition of the patient; and comparing the first output with the second output to determine the relevance of the at least one sensor of the plurality of sensors that does not transmit the at least one health condition of the patient.

9. The computer program product of claim 8, wherein each sensor of the plurality of sensors is deliberately turned off to obtain the second output for the each sensor, and wherein the comparing compares the first output with the second output for each missing sensor to determine the relevance of the each sensor of the plurality of sensors.

10. The computer program product of claim 9, wherein a sensor of the plurality of sensors is disconnected when the relevance of the sensor is less than a pre-determined threshold value.

11. The computer program product of claim 10, wherein the discriminative classifier is re-trained with a model that does not include the disconnected sensor, and wherein the relevance is determined by comparing an output from a combination of the discriminative classifier when all of the plurality of sensors are active and the generative classifier when at least one sensor of the plurality of sensors is not active.

12. The computer program product of claim 7, wherein the relevance is determined by comparing an output from a combination of the discriminative classifier when all of the plurality of sensors are active and the generative classifier when at least one sensor of the plurality of sensors is not active.

13. A recommendation system, the system comprising:
a processor; and
a memory, the memory storing instructions to cause the processor to perform:
monitoring a patient using a plurality of sensors including missing inputs as sensor failures or a sensor disconnection;
receiving patient information including a comfort level corresponding to a sensor of the plurality of sensors;
determining a relevance of each sensor of the plurality of sensors to at least one health condition of the patient; and
determining at least one sensor of the plurality of sensors to disconnect based on the comfort level and the relevance of each sensor, wherein a machine learning system determines the at least one sensor being an optimal sensor, wherein a discriminative classifier and a generative classifier are used in combination to operate concurrently with the machine learning system to consider the missing inputs to make a prediction of the relevance of each sensor regardless of the missing inputs, further comprising disconnecting the at least one sensor of the plurality of the sensors based on a result of the determining, wherein an output of the generative classifier is analyzed to turn off a sensor, and wherein the machine learning system is trained by deliberately turning off inputs in a systematic way to train the generative classifier and then a performance after turning off inputs is compared to the discriminative classifier.

14. The system of claim 13, wherein the determining the relevance determines the relevance by:

obtaining a first output using the discriminative classifier when all of the plurality of sensors transmit the at least one health condition of the patient;

obtaining a second output using the generative classifier when at least one sensor of the plurality of sensors does not transmit the at least one health condition of the patient; and comparing the first output with the second output to determine the relevance of the at least one sensor of the plurality of sensors that does not transmit the at least one health condition of the patient.

15. The system of claim 14, wherein each sensor of the plurality of sensors is deliberately turned off to obtain the second output for each sensor, and wherein the comparing compares the first output with the second output for each missing sensor to determine the relevance of the each sensor of the plurality of sensors.

16. The system of claim 15, wherein a sensor of the plurality of sensors is disconnected when the relevance of the sensor is less than a pre-determined threshold value.

17. The system of claim 16, wherein the discriminative classifier is re-trained with a model that does not include the disconnected sensor, and wherein the relevance is determined by comparing an output from a combination of the discriminative classifier when all of the plurality of sensors are active and the generative classifier when at least one sensor of the plurality of sensors is not active.

18. The system of claim 13, wherein the relevance is determined by comparing an output from a combination of the discriminative classifier when all of the plurality of sensors are active and the generative classifier when at least one sensor of the plurality of sensors is not active.

19. The system of claim 13, embodied in a cloud-computing environment.

* * * * *